United States Patent [19]

Kude et al.

[11] Patent Number: 4,632,572
[45] Date of Patent: Dec. 30, 1986

[54] IMPURITY COMPENSATION FOR COLORIFIC CONTENT ANALYZER

[75] Inventors: William B. Kude, Plymouth; A. Noel J. Pearman, St. Paul, both of Minn.

[73] Assignee: Honeywell Inc., Minneapolis, Minn.

[21] Appl. No.: 672,726

[22] Filed: Nov. 19, 1984

Related U.S. Application Data

[62] Division of Ser. No. 433,181, Oct. 6, 1982, Pat. No. 4,511,262.

[51] Int. Cl.$^4$ ............................................. G01N 25/22
[52] U.S. Cl. .......................................... 374/37; 422/97
[58] Field of Search .............................. 374/37, 36, 31

[56] References Cited

U.S. PATENT DOCUMENTS

| 4,337,654 | 7/1982 | Austin et al. | 374/37 |
| 4,351,614 | 9/1982 | Garnier | 374/37 |
| 4,382,698 | 5/1983 | Szonntagh | 374/37 |
| 4,386,858 | 6/1983 | Kude et al. | 374/37 |
| 4,396,299 | 8/1983 | Clingman, Jr. et al. | 374/37 |

Primary Examiner—Daniel M. Yasich
Attorney, Agent, or Firm—Charles G. Mersereau; Mitchell J. Halista

[57] ABSTRACT

Impurity compensation for compensating the analysis of the calorific content for fuel having an unknown amount of a known additional constituent of interest (impurity) is disclosed. In the illustrative embodiment oxygen is the impurity. In that embodiment, the fuel containing the impurity is combusted to achieve substantially stoichiometric combustion by varying the air/fuel ratio supplied to a combustion means by a rotary speed controlled in response to the sensing of oxygen in the combustion products. A first measurement of the calorific content is made using a normal operation of the analyzer and a second measurement is made using a known amount of air added to the combustible gas stream. The true air/fuel ratio and the calorific content is then computed using a predetermined relationship among the system variables.

14 Claims, 3 Drawing Figures

IMPURITY COMPENSATION FOR COLORIFIC CONTENT ANALYZER

This application is a division of application Ser. No. 433,181, filed Oct. 6, 1982, now U.S. Pat. No. 4,511,262.

CROSS-REFERENCE TO CO-PENDING APPLICATION

Subject matter disclosed but not claimed herein is shown and claimed in U.S. Pat. No. 4,386,858 issued on June 7, 1983 and assigned to the same assignee as the present application.

BACKGROUND OF THE INVENTION

1. Field Of The Invention

The present invention relates to gas analyzers. More specifically, the present invention is directed to analyzers for determining the calorific content of a combustible gas.

2. Description Of The Prior Art

The measurement of calorific content, e.g., BTU content, of a combustible gas such as that supplied for home heating by a public utility, etc., provides a measure of the quality of the gas being supplied and, hence, the appropriate rate or cost for the gas can be billed by the public utility to a customer who formerly was charged a rate based simply on a cubic volume of gas consumption. Conventional gas analyzers for determining the composition of an unknown gas have usually involved a variety of time consuming methods. The basic prior art analyzer is known as the Orsat type and is used to absorb the constituent gases one at a time from a gas mixture and to determine the constituent quantities from a resulting decrease in the gas pressure exhibited by the mixture. The resulting gas analysis could be used as a basis for consumer billing. In another apparatus, chromatographic analysis of the gas constituents has been used to compute the actual heating value or calorific content of a combustible gas from the percentage composition of the combustible constituents of the mixture. In still another device, the heat content of the gas has been determined by measuring the amount of heat liberated in burning one cubic foot of the gas in a closed volume at standard conditions of temperature and pressure. The heat so liberated is absorbed by a known quantity of surrounding water, and the subsequent temperature rise of the water is used to calculate the heating value. However, all such prior art devices are wholly impractical for mass installation on-line in gas consumer locations particularly home consumers, since such methods involve expensive instrumentation and considerable labor to perform the measurements and calculations while introducing substantial time delays. Accordingly, it is desirable to have a so-called on-line system which can measure the calorific content of the combustible gas in an unattended location and which is suitable for mass installations. Known gas analyzers of this latter type include ones based on the use of the thermal conductivity of the known gas which gas is analyzed by comparing its rate of thermal conductivity with that of a standard reference gas. Another prior art gas analyzing device uses a catalyzing wire which has its temperature affected by a gas being burned adjacent to the wire to produce an output signal which is used to ascertain the percentage of combustible gas in the gas being tested. An additional group of gas analyzers are based on an optical analysis of the color, etc., of a gas flame to provide a measure of combustible gas content. However, all of these prior art devices have serious shortcomings in providing a rapid and accurate measurement of the calorific content of the combustible gas while utilizing a compact and simple structure suitable for mass production, on-line installation and capable of being used over extended periods of time without significant maintenance.

SUMMARY OF THE INVENTION

To overcome the aforesaid defficiencies of the known methods of calculating the heat content of a combustible gas, a system has been developed using an electrochemical cell as an oxygen or combustible product sensor to sense the residual products of combustion based on ceramic compounds such as $ZrO_2$. Under normal conditions, the combustible gas is burned with excessive oxygen to assure complete combustion and an absence of carbon monoxide in the products of combustion. This leads to the presence of an amount of excessive oxygen after combustion indicates that such an oxygen sensor could provide a relatively inexpensive and rapid solution into the problem of determining the heat values for the combustible gas mixture based on the air-fuel ratio. Thus, such a system uses a ceramic based electrochemical sensor which is known to exhibit a Nernstein voltage output when exposed to different partial pressures of oxygen on each side of the ceramic material. Such a sensor can be used to sense the amount of oxygen present in the products of combustion. This system proposes to utilize a known volume ratio between the fuel and oxygen supplied to a burner in conjunction with a measurement of excess oxygen after combustion using the aforesaid Nernstein relationship to provide a basis for deriving the heat content of the fuel. This system eliminates both the need for precise temperature control of the sensor and the errors introduced by inert constituents of the combustible gas mixture.

The heat content measuring system includes a volumetric measuring system to accurately proportion the fuel which is mixed with the air. A single burner in combination with the oxygen sensing system provides the necessary air-fuel information necessary to effect a determination of the heat content measurement of the fuel gas. The system is designed to control combustion substantially at the stoichiometric point wherein the electrochemical sensor exhibits a step-change function to produce increased accuracy. At this point, the precise volumetric ratio of fuel to air is accurately known from the fuel-air ratio controlling system, and the heat content of the fuel can be accurately determined from that ratio in a manner which is simplified by the elimination of the effects of several undesirable variables. Thus, this heat content measuring system includes a precise and adjustable metering system which accurately proportions the amount of fuel gas or calorific gas to be tested with a known amount of air such that any given time, the volumetric ratio of air to fuel is precisely known.

The mixture is fed to a combustion system in which the fuel is combusted in the presence of a solid state ceramic electrochemical cell which provides a step-change in its output voltage as the amount of residual oxygen in the products of combustion approaches zero, i.e., as the combustion approaches the point of stoichiometry. An electrical output signal from the electrochemical cell is utilized with a programmable electronic processing system to adjust the fuel-air mixture in accordance with the output of the electrochemical cell to achieve the stoichiometric air-fuel ratio as signalled by the rapid change in electrical output of the cell at that point. The air-fuel ratio at that point is known from the measuring system and, therefore, the heat content of the fuel can be readily determined therefrom. However, in the blending of a combustible gas by a gas supplier, e.g., a gas utility, it is common to add air to the blend to lower the BTU value of the gas supplied to the consumer. The added oxygen contained in the mixture produces in a calorific content analyzer using the aforesaid method an error in its determination of the calorific content of the fuel in proportion to the amount of oxygen added. This occurs as a result of the oxygen in the fuel which is not accounted for by the means for providing the variable ratios of the fuel and oxygen whereby the determination of the air to fuel ratio is erroneous. Accordingly, it is desirable to provide a compensation for the fuel entrained oxygen in the determination of the calorific content of the combustible gas.

An object of the present invention is to provide an improved combustible gas calorific content analyzer having fuel entrained oxygen compensation.

In accomplishing this and other objects, there has been provided, in accordance with the present invention a combustible gas calorific content analyzer having a fuel entrained oxygen compensation for a system delivering to a combustion means a variable ratio of gas and air to produce substantially stoichiometric combustion by sensing combustion products in a first mode of operation. In a second mode of operation a predetermined quantity of air is added to the gas and delivered to the combustion in a variable ratio of gas to air to produce substantially stoichiometric combustion. A monitoring of the ratios of gas to air in the first and second modes of operation yields a measurement of the calorific content of the gas according to a predetermined relationship.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
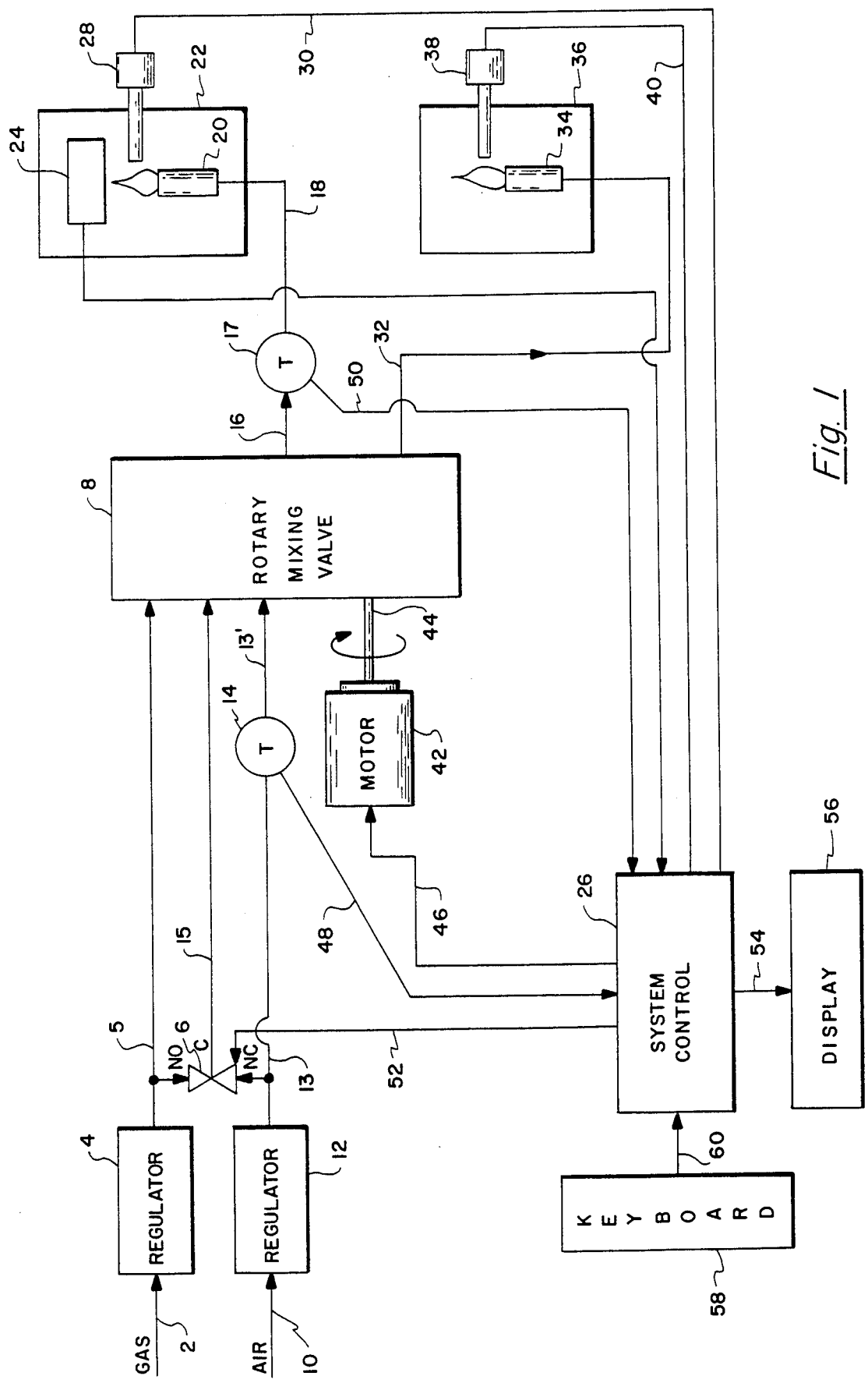
FIG. 1 is a block diagram of a calorific content analyzer utilizing an example of the present invention and FIG. 2 is an exploded pictorial illustration of a rotary mixing valve embodying an example of the present invention for use in the analyzer shown in FIG. 1

Referring to FIG. 1 in more detail, there is shown a pictorial diagram of a calorific content measuring system embodying an example of the present invention. An fuel gas inlet pipeline 2 is arranged to supply a fuel gas to a pressure regulator 4. The output of the pressure regulator 4 is applied to a solenoid controlled flow selection valve 6 and a rotary mixing valve 8. An air inlet pipeline 10 is arranged to supply combustion air to a second pressure regulator 12. The output of the second pressure regulator 12 is applied to a first input of the selection valve 6 and through a temperature measuring device 14 to a first input of a rotary mixing valve 8. The output of the selection valve 6 is supplied through pipeline 15 to a second input of the rotary mixing valve 8. A first output from the rotary mixing valve 8 is supplied through pipeline 16 to a temperature measuring device 17. The output of the temperature measuring device 17 is supplied through pipeline 18 to a burner 20 located in a primary or measuring combustion chamber 22.

An electrochemical combustion product sensor 24 is located in the combustion chamber 22 for sensing the combustion products from the burner 20. An output signal from the sensor 24 is connected to a first input of a system control apparatus 26. The system control 26 may be any suitable device for producing an output in response to a predetermined relationship of input signals applied thereto, e.g., a microprocessor operating under control of a fixed store program, such devices being well-known in the art. A first ignition and flame safeguard device 28 is also located in the combustion chamber 22 and is controlled over signal line 30 by the system control 26 to effect ignition of the burner 20 and to sense the presence of a burner flame. A second output from the rotary mixing valve 8 is connected through pipeline 32 to a second burner 34 located in a second or flare combustion chamber 36. A second ignition and flame safeguard device 38 is located in the second combustion chamber 34 and is controlled by the system control 26 over signal carrying line 40. A motor 42 is arranged to drive the rotary mixing valve 8 by a motor shaft 44 connected therebetween. The motor 42 is energized by the system control 26 over a signal carrying line 46 connected to a first output of system control 26 and may be any suitable drive device capable of being precisely controlled for rotational speed, e.g., a stepping motor.

The first temperature measuring device 14 is connected by a signal carrying line 48 to a second input of the system control 26 while the second temperature measuring device 17 is connected by a signal carrying line 50 to a third input of the system control 26. A second output from the system control 26 to the electrically control selection valve 6 is applied by a signal carrying line 52. A third output from the system control 26 is connected by a signal carrying line 54 to a display 56 for displaying the calorific content of the combustible fuel gas being tested, e.g., BTU content. A keyboard 58 connected to the system control 26 by a signal carrying line 60 is provided to supply control signals to the system control 26 which as previously mentioned may include a microprocessor having a memory for storing control signals as digital words therein.

MODE OF OPERATION

In the embodiment of the invention shown in FIG. 1, fuel and air from pressure regulators 4, 12, respectively, are fed through a rotary mixing valve 8 in which the proportion of air to fuel gas transferred therethrough to the primary or measurement combustion chamber 22 depends on the speed of rotation of the rotary valve 8. The rotary mixing valve 8 contains hollow chambers or transfer buckets in a rotor driven by the motor 42 which are alternately filled with fuel and purged with air as they are rotated past a fixed plate having first slots therein supplied with the fuel gas and air for filling the buckets, and second slots for receiving the fuel gas and air from the buckets and which are connected to the primary and secondary combustion chambers, 22, 36, respectively, as described more fully hereinafter with respect to FIGS. 2 and 3. The fixed volume slots and buckets are arranged to interact in a manner whereby the air flow remains constant and the fuel gas introduced varies with the angular speed of the rotor whereby the air-fuel ratio of the mixture supplied to the measurement combustion chamber 22 is controlled by the rotational speed of the rotor.

The motor 42 driving the rotor is speed controlled by the system control 26 to allow for flexibility in adjusting the rotational speed of the rotor and, thus, the air-fuel ratio to achieve substantially stoichiometric combustion. Specifically, the oxygen sensor 24 detects the excess oxygen in the combustion products from the burner 20 and produces a step change in its output signal at substantially stoichiometric combustion. The output signal from the sensor 24 representative of the detected oxygen level is applied via a connecting wire to the system control 26. The system control 26 is arranged to respond to the output signal from the sensor 24 to produce a first controller output signal on line 46 for controlling the speed of the motor 42, and, consequently, the rotor within the valve 8. The system control 26 is also arranged to provide a second output signal on line 54 representative of the speed of the motor 42 for application to a display device 56 for providing display of the calorific content of the fuel gas, e.g., the display device 56 may be a digital display for displaying the calorific content in BTU's.

Inasmuch as fuel and air are fed to the measuring or primary burner 20 at the same regulated pressure and, if packaged together in a measuring instrument, are substantially at the same temperature, this system eliminates additional variables relating to differences in temperature and pressure which would otherwise have to be compensated for by measuring the temperature and pressure in adjusting the calculation. Temperature compensation, of course, may be provided by temperature sensors 14, 17 in the fuel mixture and pressure compensation may also be provided in a well-known monomer for applications where the maintenance of equal pressure and temperature is not feasible. Because precise volumetric measuring by the rotary valve 8 is used, the need for compensating for changes in molecular weights or combustibles or for the addition of inert compounds is also eliminated. The calculation of the heat content of the combustible gas is made by utilizing a microprocessor system operating in accordance with a fixed stored program to solve a predetermined equation from a simplified known constant relationship between the air-fuel ratio at substantially the stoichiometric point which is known from the speed of the sampling or mixing system and the corresponding fuel heat content. The results are subsequently recorded or displayed in a suitable manner. The aforesaid system, however, has a disadvantage in that the combustible fuel gas often contains entrained oxygen which provides oxygen for combustion with the combustible gas constituents at the burner in addition to the oxygen provided by the air supply. Thus, by utilizing the straightforward application of the air-fuel ratio, the deviation produced by the entrained oxygen in the combustible gas is not accounted for which produces an error in the calorific content measurement since the rotary valve speed is faster than that which would be required for the same fuel gas without entrained oxygen inasmuch as the entrained oxygen displaces fuel gas.

This error can be corrected by making two measurements of the unknown combustible gas. The first measurement is taken in the normal way as described above using the calorific content analyzer, and the speed of the rotary valve providing the variable air-fuel ratio for substantially stoichiometric combustion is controlled and stored in the system control 26. The second measurement is made when substantially stoichiometric combustion is attained with a known amount of air added to the unknown combustible gas stream. The true air/fuel ratio can then be computed by the system control 26 using the following equation.

$$K = \frac{T_F}{T_A} \frac{Q_A}{K_r \cdot C_{o/2}} \left( \frac{1}{f_1} - \frac{1}{f_2} \right) - 1$$

Where:
$C_{o/2}$ = known concentration of air added to fuel
$f_1$ = measured result without $C_{o/2}$
$f_2$ = measured result with $C_{o/2}$
$T_F$ = temperature fuel
$T_A$ = temperature air
$C_o$ = concentration of oxygen in moist air
$K_r$ = rotary valve gain constant
$K$ = air/fuel ratio
$Q_a$ = air volumetric flow rate This equation is derived from an analyzer system model analysis with oxygen in fuel and without oxygen in fuel with a final subtraction of the two descriptive equations. The problem accordingly reduces to one of introducing an accurately measured oxygen concentration into the gas stream and producing a substantially stoichiometric combustion of the resulting mixture. This problem is solved by adding an additional set of transfer buckets to the rotor of the rotary valve 8.

Figure 2:
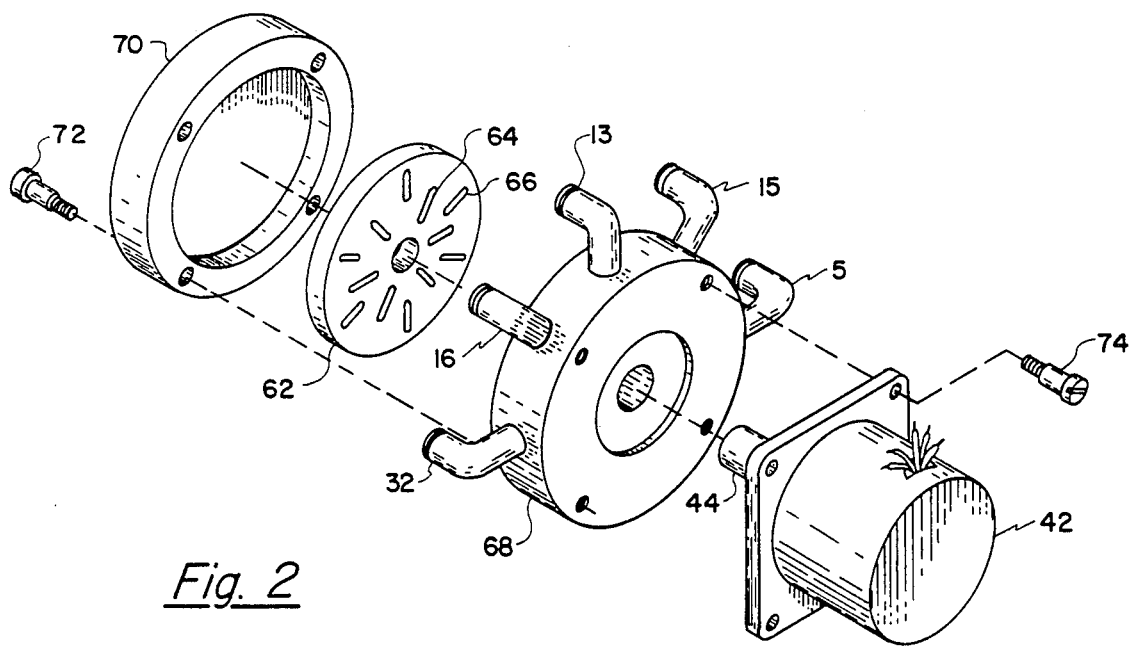

In FIG. 2, there is shown an exploded pictorial illustration of a rotary mixing valve for use with the present invention. The rotary mixing valve includes a motor 42 having an output shaft 44 connected to a rotor 62. The rotor 62 has surface depressions forming chambers of fluid carrying transfer buckets 64 located in its surface with a first group of chambers or buckets 64 being located at a first radial distance from the center of the rotor 62 and the second group of buckets 66 being located at a second radial distance from the center of the rotor 62. A fixed plate or stator 68, described more fully hereinafter, is connected to the motor 42 and is used to provide the connections for the pipelines 5, 13, 15, 16 and 32 shown in FIG. 1. A cover 70 is arranged to cover the rotor 62 and is attached to the stator 68 by any suitable means such as machine screws 72. Finally, the layered package of the rotor, the stator 68 and the cover 70 is attached to the motor 42 by any suitable means such as machine screws 74 to form a layered structure.

Figure 3:
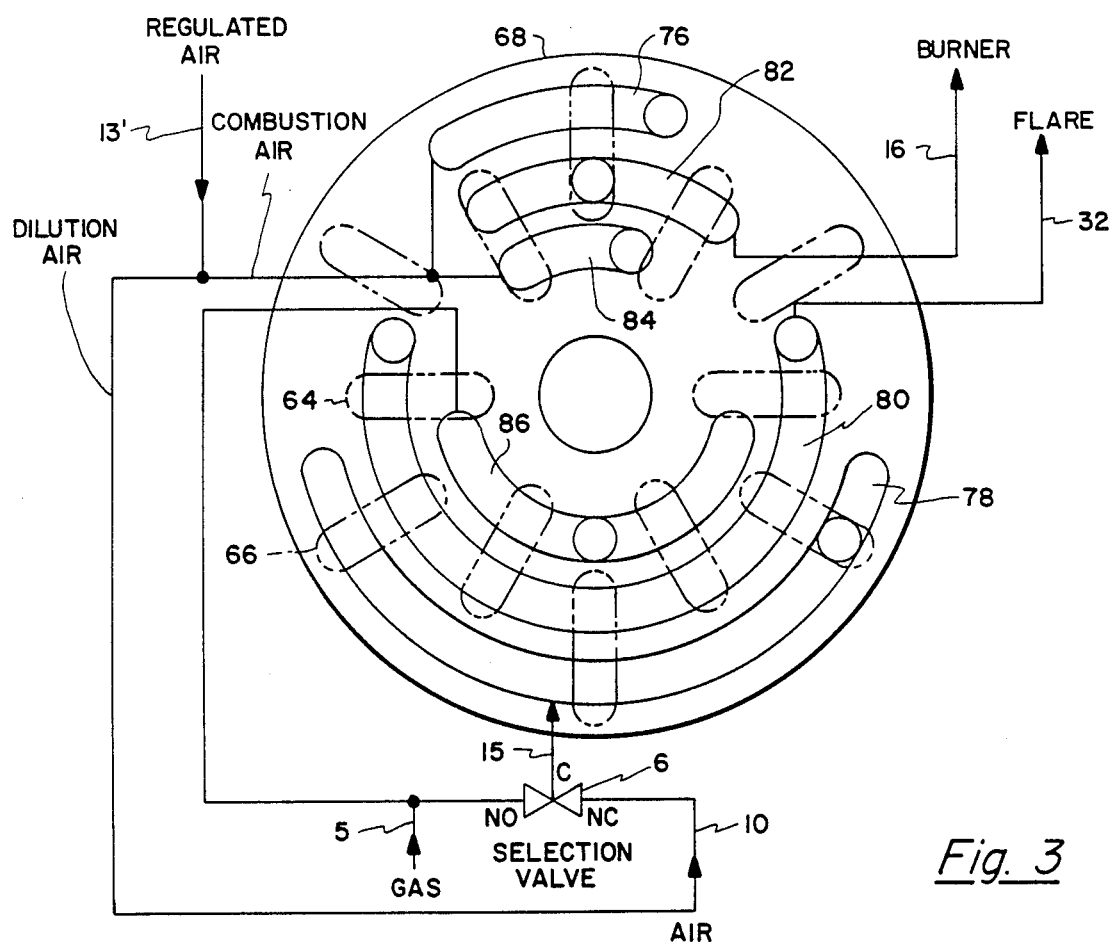
FIG. 3 is a pictorial illustration of the face of the fixed plate used in rotary mixing valve shown in FIG. 2.

In FIG. 3, there is shown a front view of the face of the stator 68 adjacent to the face of the rotor 62 having the transfer buckets 64, 66 therein. As shown in this view, the face of the stator 68 has three groups of coaxial slots or grooves therein for supplying and receiving gases. Thus, some of the slots receive air or fuel gas supplied to the rotary valve 8 for application to the buckets 64, 66 while other ones of the slots supply air and gas to the main burner 82 and the flare burner 80 after receiving the air and gas from the buckets 64, 66. A first group of slots 76, 78 are arranged at an outer radius from the center of the stator 68 while a second group of slots 80 and 82 are arranged at an intermediate radius from the center of the stator 68. A third group of slots 84, 86 are arranged at an inner radius from the center of the stator 68. Of the longer slots 78, 80 and 86 in the face of the stator 68, slots 78 and 86 encompass approximately 153° while the intermediate slot 80 covers approximately 208°. Of the shorter slots 76, 82, 84 in the face of the plate 68, slots 76 and 84 cover approximately 49° while intermediate slot 82 covers approximately 70°. Thus, the air receiving slots 76 and 84 are shorter than either the fuel gas receiving slot 86 or the selective air-gas receiving slot 78. Similarly, the main burner supply slot 82 is shorter than the flare or secondary burner supply slot 80. Internal drillings (not shown) in the stator 68 connect the slots 76 and 84 to pipeline 13 and slots 78, 80, 82, and 86 to pipelines 5, 15, 16 and 32. The relationship of the slots 76 and 84 to pipeline 13 and slots 78, 80, 82, 84 and 86 in the face of the stator 68 and the groups of transfer buckets 64 and 66 in the rotor 62 are shown in FIG. 3 by a phantom representation of the groups of buckets 64 and 66. The rotor 62 is urged against the stator 68 to provide a substantially fluid-tight seal between the contacting faces thereof having the buckets 64, 66 and the slots 76, 78, 80, 82, 84 and 86 therein. This seal may be enhanced by coating the contacting faces of the rotor 62 and the stator 68 with a low friction material, e.g., polytetrafluoroethylene.

To make the initial measurement, the selection valve 6 is set to enable fuel gas purging of the outer buckets. The total volume of gas transferred by each bucket pair is:

$$V_T = V_1 + V_2$$

Where
$V_1$ = buckets 64 volume
$V_2$ = buckets 66 volume

The normal operation of the calorific content analyzer then results in the determination of $f_1$ based on the required rotary valve motor speed needed to achieve substantially stoichiometric combustion. After $f_1$ has been determined, the selection valve 6 is switched to enable air purging of the outer transfer buckets 66. On the other hand, fuel gas purging is maintained on the inner buckets 64. The concentration of air added to the fuel gas when the rotary valve dumps the transfer buckets 64 and 66 into the primary or measurement burner 20 is proportional to the ratio of $V_2/(V_1+V_2)$. The concentration of the air added to the gas is fixed by the size of the transfer buckets 64, 66 and therefore is known by:

$$C_{OF2} = \frac{V_2}{V_1 + V_2}$$

The true calorific content value of the fuel gas can then be determined by solving the first equation shown above where $f_2$ is found by determining the rotary valve motor speed required for substantially stoichiometric combustion with the added air. In the actual operation of the analyzer, the value of $C_{OF2}$ would be determined by means of a calibration gas of known calorific content. This calibration gas would be measured during substantially stoichiometric combustion with and without the added air to indirectly determine $C_{OF2}$.

Accordingly, it may be seen that there has been provided, in accordance with the present invention a calorific content analyzer having compensation means for fuel entrained oxygen.

The embodiments of the invention in which an exclusive property or privilege is claimed are defined as follows:

1. A method of determining the heating value of impure gaseous fuels containing an unknown amount of a known additional constituent of interest (impurity) comprising the steps of:
    establishing a first mixture of the impure fuel and air of known proportions;
    oxidizing said first mixture of known proportions;
    sensing the products of combustion of said mixture with a sensor having an output with a peak sensitivity at a known percentage composition of a known control constituent in the products of oxidation;
    adjusting the proportions of impure fuel and air in said first mixture based on the output of said sensor until said control constituent is at said known percentage;
    determining the fuel to air ratio of said first mixture at said control constituent percentage from a known relationship between the heating value of the fuel and the amount of oxygen required for stoichiometric oxidation thereof;
    establishing a second mixture of said impure fuel and air of known proportions into which a known additional amount of said impurity is introduced;
    oxidizing said second mixture of known proportions;
    sensing the products of combustion of said second mixture with said sensor;
    adjusting the proportions of impure fuel and air in said second mixture based on the output of said sensor until said control constituent is at said known percentage;
    determining the fuel to air ratio of said second mixture in the manner of said first mixture;
    determining the heating value of said impure fuel from a known relationship between the stoichiometric fuel to air ratios of both of said first and second mixtures and the heating value of said gaseous fuel and the heating value (positive or negative) of said impurity.

2. The method of claim 1 wherein said impure fuel contains a plurality of impurities and comprising the additional steps of:
    sequentially with respect to each of said plurality of of impurities establishing additional mixtures of said impure fuel and air of known proportions each of said additional mixtures containing a known additional amount of a different one of said impurities;
    oxidizing each of said additional mixtures;
    sensing the products of combustion of each of said mixture with said sensor;
    adjusting the proportions of impure fuel and air in each of said additional mixtures based on the output of said sensor until said control constituent is at said known percentage;
    determining the fuel to air ratio of each of said impure fuel mixtures in the manner of said first mixture;
    determining the heating value of said impure fuel from a known relationship between the stoichiometric fuel to air ratios of said first, said second and each additional of said plurality mixtures and the heating value of said gaseous fuel and the heating value (positive or negative) of each said impurity.

3. The method of claim 2 wherein said control constituent is oxygen.

4. The method of claim 2 wherein one of said impurities is oxygen.

5. The method of claim 4 wherein the additional amount of impurity is added in the form of air.

6. The method of claim 2 wherein one of said impurities is a combustible constituent.

7. The method of claim 6 wherein said combustible constituent is $H_2$.

8. The method of claim 6 wherein said combustible constituent is CO.

9. The method of claim 1 wherein said control constituent is oxygen.

10. The method of claim 1 wherein said impurity is oxygen.

11. The method of claim 10 wherein the additional amount of impurity is added in the form of air.

12. The method of claim 1 wherein said impurity is a combustible constituent.

13. The method of claim 12 wherein said impurity is $H_2$.

14. The method of claim 12 wherein said impurity is CO.

* * * * *